US008956605B2

(12) United States Patent
Huang et al.

(10) Patent No.: US 8,956,605 B2
(45) Date of Patent: Feb. 17, 2015

(54) PREVENTION AND/OR TREATMENT OF MULTIPLE ORGAN DYSFUNCTION SYNDROME WITH INTERLEUKIN-22

(75) Inventors: Yu Liang Huang, Shanghai (CN); Zhi Hua Huang, Shanghai (CN); Qi Sun, Shanghai (CN)

(73) Assignee: Generon (Shanghai) Corporation, Shanghai (CN)

( * ) Notice: Subject to any disclaimer, the term of this patent is extended or adjusted under 35 U.S.C. 154(b) by 0 days.

(21) Appl. No.: 13/142,423

(22) PCT Filed: Jan. 11, 2010

(86) PCT No.: PCT/US2010/020673
§ 371 (c)(1),
(2), (4) Date: Jun. 28, 2011

(87) PCT Pub. No.: WO2010/081112
PCT Pub. Date: Jul. 15, 2010

(65) Prior Publication Data
US 2011/0268696 A1 Nov. 3, 2011

Related U.S. Application Data

(60) Provisional application No. 61/144,134, filed on Jan. 12, 2009.

(51) Int. Cl.
| A61K 38/20 | (2006.01) |
| C07K 14/54 | (2006.01) |
| A61P 31/04 | (2006.01) |
| A61P 1/16 | (2006.01) |

(52) U.S. Cl.
CPC ............. *A61K 38/20* (2013.01); *A61K 38/2066* (2013.01)
USPC ............................ 424/85.2; 514/1.4; 530/351

(58) Field of Classification Search
None
See application file for complete search history.

(56) References Cited

U.S. PATENT DOCUMENTS

2003/0186387 A1* 10/2003 Ebner et al. ................. 435/69.52
2007/0207943 A1   9/2007 Ebner et al.

OTHER PUBLICATIONS

DE Papathanassoglou et al, Nursing in Critical Care 2008, vol. 13 No. 5, pp. 249-259.*
Craig et al, Alimentary Pharmacology and Therapeutics, 2009, vol. 31, pp. 345-358.*
Radaeva et al, Hepatology, 2004, vol. 39, No. 5, pp. 1335-1342.*
Rahman et al, J. Exp. Path. 2000, vol. 81, pp. 145-157.*
Zheng et al, Mar. 2008 nature medicine, vol. 14, No. 3, Feb. 2008, pp. 282-289.*
Bingold, Shock, 2010; vol. 34, No. 4, pp. 337-340.*
Rendon et a, Journal of Leukocyte Biology, vol. 92, Sep. 2012, pp. 529-538.*
Weber, Infection and Immunity, Apr. 2007, pp. 1690-16970.*
Hwang, Potential Use of Albumin Administration in Severe Sepsis, J Chin Med assoc, May 2009, vol. 72, No. 5, pp. 225-226.
Quinlan et al, Administration of albumin to patients with sepsis syndrome: a possible beneficial role in plasma thiol repletion, Clinical Science (1998), 95, pp. 459-465.
Dubois et al, Albumin administration improves organ function in critically ill hypoalbuminemic patients: A prospective, randomized, controlled, pilot study, Crit Care Med, 2006, vol. 34, No. 10, pp. 2536-2540.
Delaney et al, The role of albumin as a resuscitation fluid for patients with sepsis: A systematic review and meta-analysis, Crit Care Med 2001 vol. 39, No. 2, pp. 386-391.
Lee at al, Palmatine attenuates D-galactosamine/lipopolysaccharide-induced fulminant hepatic failure in mice, Food Chem Toxicol Jan. 2010, 48(1), pp. 222-228.
Qiu et al, Fibronectin prevents D-galactosamine/lipopolysaccharide-induced lethal hepatic failure in mice, Shock, vol. 25, No. 1, pp. 80-87, 2006.
Xing et al, Hepatoprotective effects of IL-22 on fulminant hepatic failure induced by D-galactosamine and lipopolysaccharide in mice, Cytokine, 56, 2011, pp. 174-179.
Wolk et al, IL-22 Increases the Innate Immunity of Tissues, Immunity, vol. 21, 241-254, Aug. 2004.
Jiang et al.; "IL-22 is related to development of human colon cancer by activation of STAT3"; BMC Cancer; 2013; 13:59.
Jiang et al,; "Interleukin-22 Promotes Human Hepatocellular Carcinoma by Activation of STAT3"; Hepatology, 2011; vol. 54, No. 3, 900-909.
Flynn et al,; "Tumor Necrosis Factor-alpha Is Required in the Protective Immune Response Against *Mycobacterium tuberculosis* in Mice"; Immunity; Jun. 1995; vol. 2, 561-672.
Remick et al,; "Pathophysiology of Sepsis"; Am J Pathol; 2007; 170:1435-1444.
Bone et al,; "Definitions for Sepsis and Organ Failure and Guidelines for the Use of Innovative Therapies in Sepsis"; Chest; 1992; 101:1644-55.
Naoko Satoh-Takayama et al.; "Microbial Flora Drives Interleukin 22 Production in Intestinal NKp46+ Cells that Provide Innate Mucosal Immune Defense", Immunity, Dec. 19, 2008, vol. 29, Issue 6, p. 958-970.
Lauren A. Zenewicz et al.; "Interleukin-22 but Not Interleukin-17 Provides Protection to Hepatocytes during Acute Liver Inflammation", Immunity, Oct. 26, 2007, vol. 27, Issue 4, p. 647-659.
Gan Mei et al. "The Progress of Multiple Organ Dysfunction Syndrome", Medical Recapitulate, Jul. 2006, vol. 12 No. 14, p. 862-865.

* cited by examiner

*Primary Examiner* — Bridget E Bunner
*Assistant Examiner* — Fozia Hamud
(74) *Attorney, Agent, or Firm* — Eagle IP Limited; Jacqueline C. Lui (57) ABSTRACT

The present invention relates to use an agent for the prevention and/or treatment of multiple organ dysfunction syndrome (MODS) or multiple organ failure (MOF) comprising interleukin-22 (IL-22) as an effective ingredient. The present invention is applicable to prevention of or therapy for diseases from sepsis, septic shock, liver failure, to multiple organ dysfunction syndromes. More particularly, the present invention is useful for an emergency medical service, for treatment of injury caused by a traffic accident, burns, heat attacks, hypercytokinemia or severe infective diseases.

9 Claims, 7 Drawing Sheets

Murine Interleukin-22 cDNA sequence
SEQ ID NO 1

Fig.1

Human Interleukin-22 cDNA sequence
SEQ ID NO 2

Fig.2

Murine Interleukin-22 amino acid sequence
SEQ ID NO 3

MAALQKSVSSFLMGTLATSCLL
LLALLVQGGAAAPISSHCRLDK
SNFQQPYITNRTFMLAKEASLA
DNNTDVRLIGEKLFHGVSMSER
CYLMKQVLNFTLEEVLFPQSDR
FQPYMQEVVPFLARLSNRLSTC
HIEGDDLHIQRNVQKLKDTVKK
LGESGEIKAIGELDLLFMSLRN
ACI

Fig. 3

Human Interleukin-22 amino acid sequence
SEQ ID NO 4

MAVLQKSMSFSLMGTLAASCLL
LIALWAQEANALPVNTRCKLEV
SNFQQPYIVNRTFMLAKEASLA
DNNTDVRLIGEKLFRGVSAKDQ
CYLMKQVLNFTLEDVLLPQSDR
FQPYMQEVVPFLTKLSNQLSSC
HISGDDQNIQKNVRRLKETVKK
LGESGEKAIGELDLLFMSLRNA
CV

SEQUENCE LISTING

```
<160> NUMBER OF SEQ ID NOS: 8

<210> SEQ ID NO 1
<211> LENGTH: 1147
<212> TYPE: DNA
<213> ORGANISM: Artificial Sequence
<220> FEATURE:
<223> OTHER INFORMATION: Murine

<400> SEQUENCE: 1
cgaccaggtt ctccttcccc agtcaccagt tgctcgagtt agaattgtct gcaatggccg        60
ccctgcagaa atctgtgagc tctttcctta tggggaccct ggccaccagc tgcctccttc       120
tcttggccct cttggtacag ggaggagcag ctgcgcccat cagctcccac tgcaggcttg       180
acaagtccaa cttccagcag ccctatatca ccaaccgcac cttcatgctg gctaaggagg       240
ctagcttggc tgataacaac acagacgttc gtctcattgg ggagaaactg ttccacggag       300
tcagtatgag tgagcgctgc tatctgatga agcaggtgct gaacttcaac cttgaagaag       360
tgctgttccc tcaatctgat aggttccagc cttatatgca ggaggtggtg cccttcctgg       420
ccaggctcag caacaggcta agcacatgtc atattgaagg tgatgacctg catatccaga       480
ggaatgtgca aaagctgaag gacacagtga aaagcttgg agagagtgga gagatcaaag       540
caattggaga actggatttg ctgtttatgt ctctgagaaa tgcctgcatt tgaccagagc       600
aaagctgaaa aatgaataac taacccccctt tccctgctag aaataacaat tagatgcccc       660
aaagcgattt tttttaacca aaaggaagat gggaagccaa actccatcat gatggtggga       720
ttccaaatga accctgcgt tagttacaaa ggaaaccaat gccacttttg tttataagac       780
```

```
cagaaggtag actttctaag catagatatt tattgataac atttcattgt aactggtgtt      840
ctatacacag aaaacaattt attttttaaa taattgtctt tttccataaa aaagattact      900
ttccattcct ttaggggaaa aaacccctaa atagcttcat gtttccataa tcagtacttt      960
atatttataa atgtatttat tattattata agactgcatt ttatttatat cattttatta     1020
atatggattt atttatagaa acatcattcg atattgctac ttgagtgtaa ggctaatatt     1080
gatatttatg acaataatta tagagctata acatgtttat ttgacctcaa taaacacttg     1140
gatatcc                                                               1147
```

<210> SEQ ID NO 2
<211> LENGTH: 1121
<212> TYPE: DNA
<213> ORGANISM: Artificial Sequence
<220> FEATURE:
<223> OTHER INFORMATION: Homo sapiens

<400> SEQUENCE: 2

```
cctaaacagg atatcatata acttatcaac tgttgacact tgtgcgatct ctgatggctg       60
tcctgcagaa atctatgagt tttcccctta tggggacttt ggccgccagc tgcctgcttc      120
tcattgccct gtgggccag gaggcaaatg cgctgcccgt caacacccgg tgcaagcttg       180
aggtgtccaa cttccagcag ccgtacatcg tcaaccgcac ctttatgctg gccaaggagg      240
ccagccttgc agataacaac acagacgtcc ggctcatcgg ggagaaactg ttccgaggag      300
tcagtgctaa agatcagtgc tacctgatga agcaggtgct caacttcacc ctggaagacg      360
ttctgctccc ccagtcagac aggttccagc cctacatgca ggaggtggta cctttcctga      420
ccaaactcag caatcagctc agctcctgtc acatcagcgg tgacgaccag aacatccaca      480
agaatgtcag aaggctgaag gagacagtga aaaagcttgg agagagtgga gagatcaagg      540
cgattgggga actggacctg ctgtttatgt ctctgagaaa tgcttgcgtc tgagcgagaa      600
gaagctagaa aacgaagaac tgctccttcc tgccttctaa aaagaacaat aagatccctg      660
aatggacttt tttactaaag gaaagtgaga agctaacgtc catcatcatt agaagatttc      720
acatgaaacc tggctcagtt gaaaagaaa atagtgtcaa gttgtccatg agaccagagg      780
tagacttgat aacccacaaag attcattgac aatatttat tgtcactgat gatacaacag      840
aaaaataatg tactttaaaa aattgtttga aggaggttca catatcatta ctttagaaaa      900
aaagcttatg taacttcatt tacatataca atatttttata tatgtaagtt tatttattat     960
aagtatacat tttatttatg tcagtttatt aatatggatt tatttataga aacattatct     1020
gctattgata tttagtataa ggcaaataat atttatgaca ataactatgg aaacaagata     1080
tcttaggctt taataaacac atggatatca taaaaaaaa a                          1121
```

<210> SEQ ID NO 3
<211> LENGTH: 179
<212> TYPE: PRT
<213> ORGANISM: Artificial Sequence
<220> FEATURE:
<223> OTHER INFORMATION: Murine

<400> SEQUENCE: 3

```
Met Ala Ala Leu Gln Lys Ser Val Ser Ser Phe Leu Met Gly Thr Leu
1               5                   10                  15

Ala Thr Ser Cys Leu Leu Leu Leu Ala Leu Leu Val Gln Gly Gly Ala
            20                  25                  30
```

-continued

Ala Ala Pro Ile Ser Ser His Cys Arg Leu Asp Lys Ser Asn Phe Gln
            35                  40                  45

Gln Pro Tyr Ile Thr Asn Arg Thr Phe Met Leu Ala Lys Glu Ala Ser
 50                  55                  60

Leu Ala Asp Asn Asn Thr Asp Val Arg Leu Ile Gly Glu Lys Leu Phe
65                  70                  75                  80

His Gly Val Ser Met Ser Glu Arg Cys Tyr Leu Met Lys Gln Val Leu
                85                  90                  95

Asn Phe Thr Leu Glu Glu Val Leu Phe Pro Gln Ser Asp Arg Phe Gln
            100                 105                 110

Pro Tyr Met Gln Glu Val Val Pro Phe Leu Ala Arg Leu Ser Asn Arg
            115                 120                 125

Leu Ser Thr Cys His Ile Glu Gly Asp Asp Leu His Ile Gln Arg Asn
            130                 135                 140

Val Gln Lys Leu Lys Asp Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Ile

<210> SEQ ID NO 4
<211> LENGTH: 178
<212> TYPE: PRT
<213> ORGANISM: Artificial Sequence
<220> FEATURE:
<223> OTHER INFORMATION: Homo sapiens

<400> SEQUENCE: 4

Met Ala Val Leu Gln Lys Ser Met Ser Phe Ser Leu Met Gly Thr Leu
1               5                   10                  15

Ala Ala Ser Cys Leu Leu Leu Ile Ala Leu Trp Ala Gln Glu Ala Asn
            20                  25                  30

Ala Leu Pro Val Asn Thr Arg Cys Lys Leu Glu Val Ser Asn Phe Gln
            35                  40                  45

Gln Pro Tyr Ile Val Asn Arg Thr Phe Met Leu Ala Lys Glu Ala Ser
 50                  55                  60

Leu Ala Asp Asn Asn Thr Asp Val Arg Leu Ile Gly Glu Lys Leu Phe
65                  70                  75                  80

Arg Gly Val Ser Ala Lys Asp Gln Cys Tyr Leu Met Lys Gln Val Leu
                85                  90                  95

Asn Phe Thr Leu Glu Asp Val Leu Leu Pro Gln Ser Asp Arg Phe Gln
            100                 105                 110

Pro Tyr Met Gln Glu Val Val Pro Phe Leu Thr Lys Leu Ser Asn Gln
            115                 120                 125

Leu Ser Ser Cys His Ile Ser Gly Asp Asp Gln Asn Ile Gln Lys Asn
            130                 135                 140

Val Arg Arg Leu Lys Glu Thr Val Lys Lys Leu Gly Glu Ser Gly Glu
145                 150                 155                 160

Lys Ala Ile Gly Glu Leu Asp Leu Leu Phe Met Ser Leu Arg Asn Ala
                165                 170                 175

Cys Val

<210> SEQ ID NO 5
<211> LENGTH: 22
<212> TYPE: DNA
<213> ORGANISM: Artificial Sequence -continued

```
<220> FEATURE:
<223> OTHER INFORMATION: Sense primer

<400> SEQUENCE: 5
gcagaatctt cagaacaggt tc                                                22

<210> SEQ ID NO 6
<211> LENGTH: 22
<212> TYPE: DNA
<213> ORGANISM: Artificial Sequence
<220> FEATURE:
<223> OTHER INFORMATION: Anti-sense primer

<400> SEQUENCE: 6
ggcatctaat tgttatttct ag                                                22

<210> SEQ ID NO 7
<211> LENGTH: 22
<212> TYPE: DNA
<213> ORGANISM: Artificial Sequence
<220> FEATURE:
<223> OTHER INFORMATION: Sense primer

<400> SEQUENCE: 7
ctctcactta tcaactgttg ac                                                22

<210> SEQ ID NO 8
<211> LENGTH: 23
<212> TYPE: DNA
<213> ORGANISM: Artificial Sequence
<220> FEATURE:
<223> OTHER INFORMATION: Anti-sense primer

<400> SEQUENCE: 8
gatgatggac gttagcttct cac                                               23
```

PREVENTION AND/OR TREATMENT OF MULTIPLE ORGAN DYSFUNCTION SYNDROME WITH INTERLEUKIN-22

FIELD OF INVENTION

This invention relates to the medical use of Interleukin-22 (IL-22).

BACKGROUND OF INVENTION

Multiple organ dysfunction syndrome (MODS), previously known as multiple organ failure (MOF), is altered organ function in an acutely ill patient such that homeostasis cannot be maintained without medical intervention. It is well established that Systemic Inflammatory Response Syndrome (SIRS) will lead to sepsis or severe sepsis and eventually lead to MODS. MODS usually results from uncontrolled inflammatory response which is triggered by infection, injury (accident or surgery), hypoperfusion and/or hypermetabolism. The uncontrolled inflammatory response will lead to SIRS or sepsis.

SIRS is an inflammatory state affecting the whole body. It is one of several conditions related to systemic inflammation, organ dysfunction, and organ failure. SIRS is a subset of cytokine storm, in which there is abnormal regulation of various cytokines. The cause of SIRS can be classified as infectious or noninfectious. SIRS is also closely related to sepsis. When SIRS is due to an infection, it is considered as sepsis. Noninfectious causes of SIRS include trauma, burns, pancreatitis, ischemia and hemorrhage. Sepsis is a serious medical condition characterized by a whole-body inflammatory state. Sepsis can lead to septic shock, multiple organ dysfunction syndrome and death. Both SIRS and sepsis could ultimately progress to MODS.

The underline mechanism of MODS is not well understood. At present there is no agent that can reverse the established organ failure. Therapy therefore is limited to supportive care. Prevention and treatment for MODS, MOF or sepsis are important to emergency medical service, for treatment of injury caused by traffic accident, burns, heart attacks, and severe infective diseases. Therefore, the development of an effective drug is in urgent need for patients.

SUMMARY OF INVENTION

It is therefore an object of the present invention to provide a therapeutic composition and method for MODS, MOF or sepsis.

Accordingly, the present invention, in one aspect, provides the use of interleukin-22 IL-22) in manufacture of a composition for preventing and/or treating MODS, MOF, sepsis, or liver failure.

In another aspect, the present invention provides a method for the prevention and the treatment of MODS, MOF, sepsis, or liver failure in a subject, the method comprising administering a pharmaceutically effective amount of IL-22. In a further aspect, the present invention relates to the use of IL-22 in the manufacture of a medicament for preventing and treating MODS, MOF, sepsis, or liver failure. MODS, MOF or sepsis may be caused by, among other causes, trauma such as traffic accidents, burns, heart attack, and severe infective diseases.

In various aspects, IL-22 of the present invention includes but is not limited to mammal IL-22 and recombinant mammal IL-22. In a preferred embodiment, IL-22 is human IL-22.

DETAILED DESCRIPTION OF THE PREFERRED EMBODIMENTS

Example 1

Human and Murine IL-22 Gene Cloning

Cloning of human IL-22 gene: Human peripheral blood monocytes were stimulated with anti-human $CD_3$ mAb and cultured for 24 h. Total RNA was extracted by ultracentrifugation, and cDNA was synthesized with the dT primers. Human IL-22 gene was amplified by PCR with the sense primer (5'-GCA GAA TCT TCA GAA CAG GTT C-3', SEQ ID NO 5) and anti-sense primer (5'-GGC ATC TAA TTG TTA TTT CTA G-3', SEQ ID NO 6). The amplified DNA is cloned into E. coli expression vector.

Cloning of mouse IL-22 gene: C57BL/6 female mice were injected with LPS (5 mg/kg, sc). The spleen was obtained after 20 hours. Total RNA was extracted and cDNA was synthesized with the dT primers. Mouse IL-22 gene was amplified by PCR with the sense primer (5'-CTC TCA CTT ATC AAC TGT TGA C-3', SEQ ID NO 7) and anti-sense primer (5'-GAT GAT GGA CGT TAG CTT CTC AC-3', SEQ ID NO 8). The amplified cDNA was cloned into E. coli expression vector pET21(+).

Figure 1:
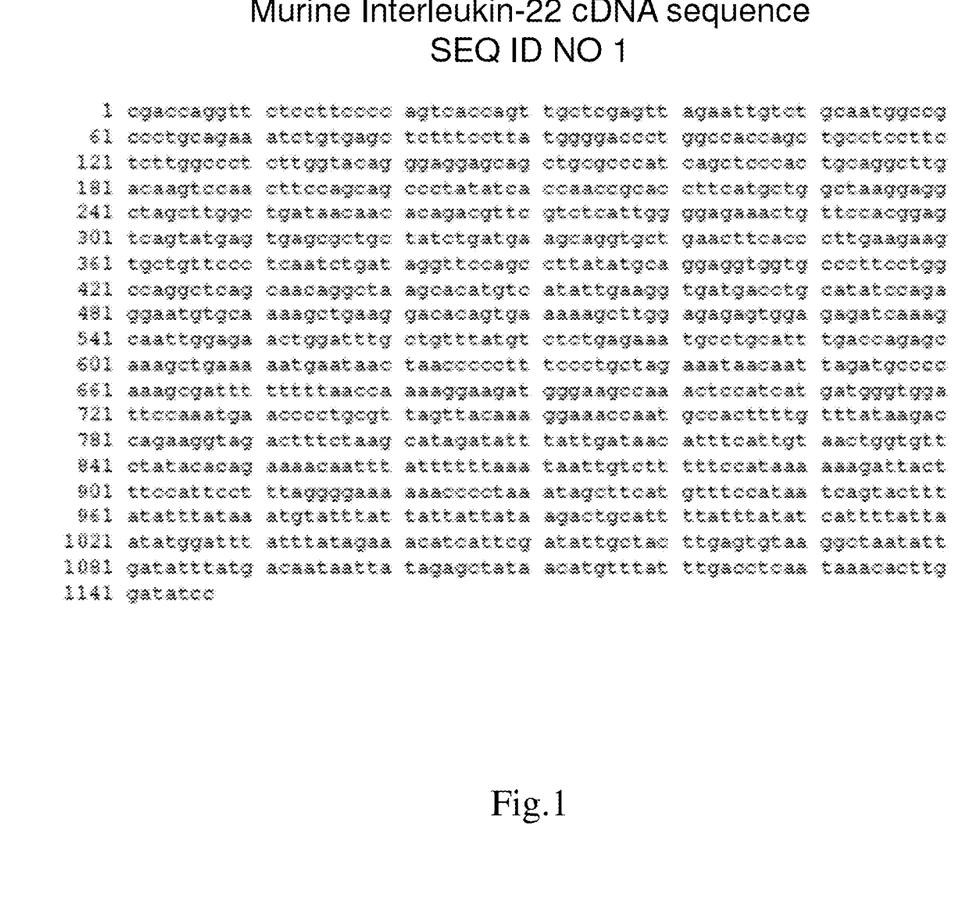
FIG. 1 shows the Murine interleukin-22 cDNA sequence.
Figure 2:
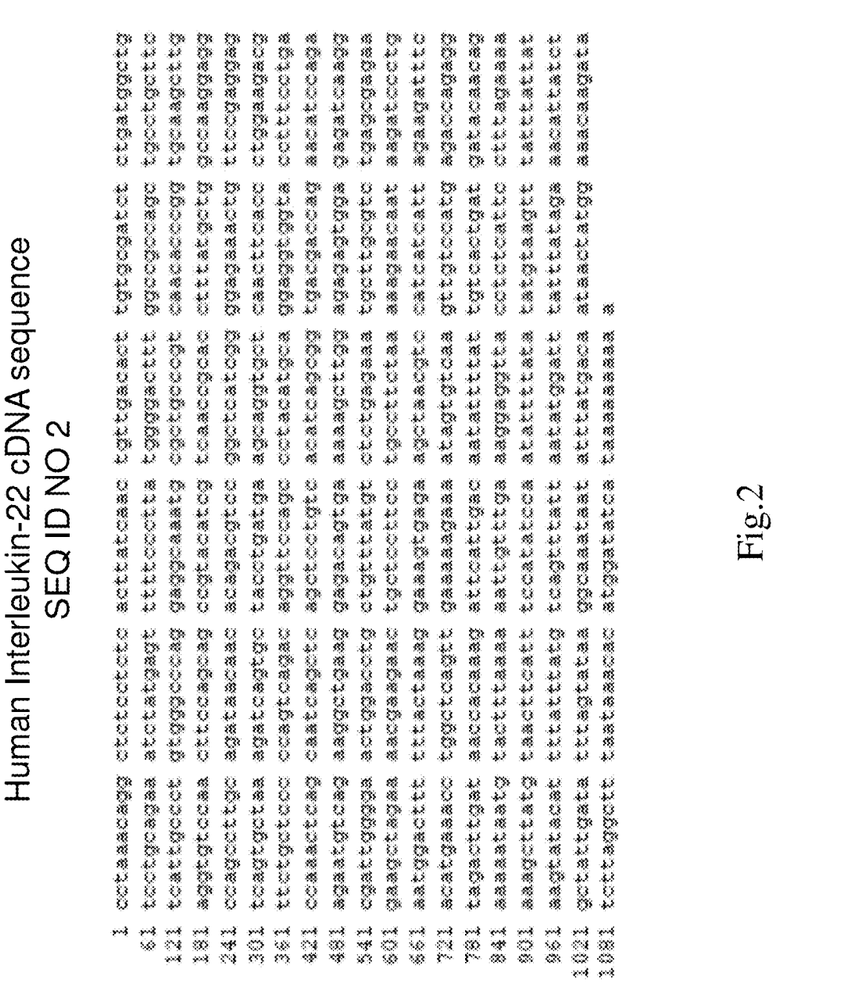
FIG. 2 shows the Human interleukin-22 cDNA sequence.

Both human IL-22 and murine IL-22 were verified by DNA sequencing, as shown in FIG. 1 and FIG. 2.

Example 2

Human IL-22 and Mouse IL-22 Gene Expression

Figure 3:
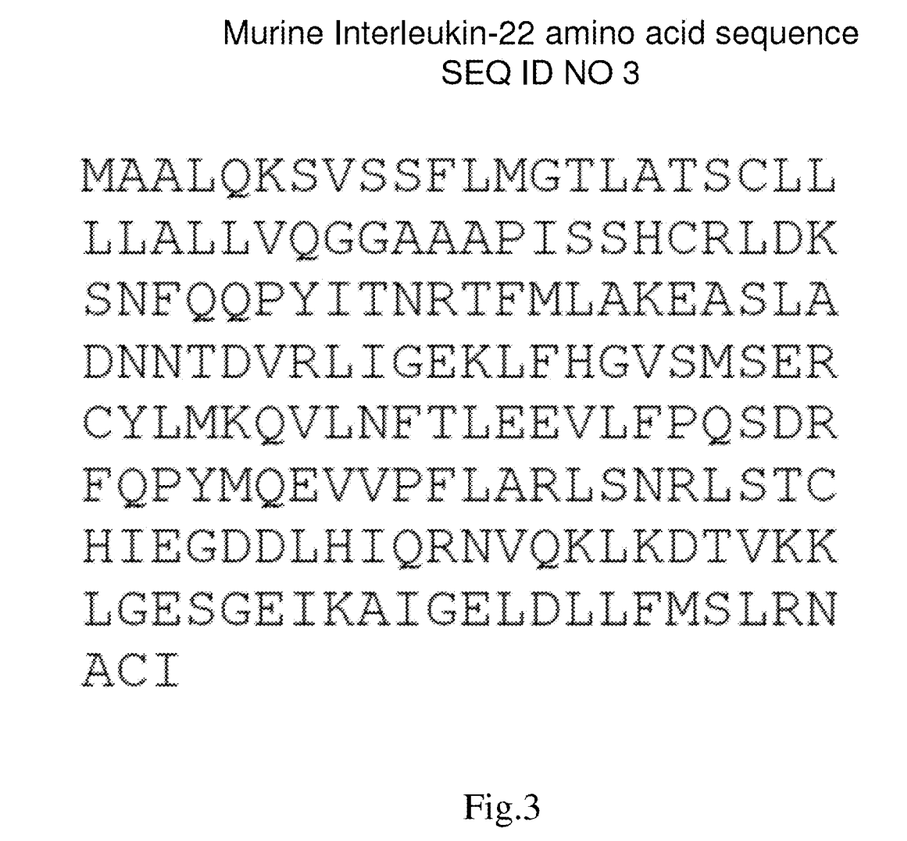
FIG. 3 shows the Murine interleukin-22 amino acid sequence.
Figure 4:
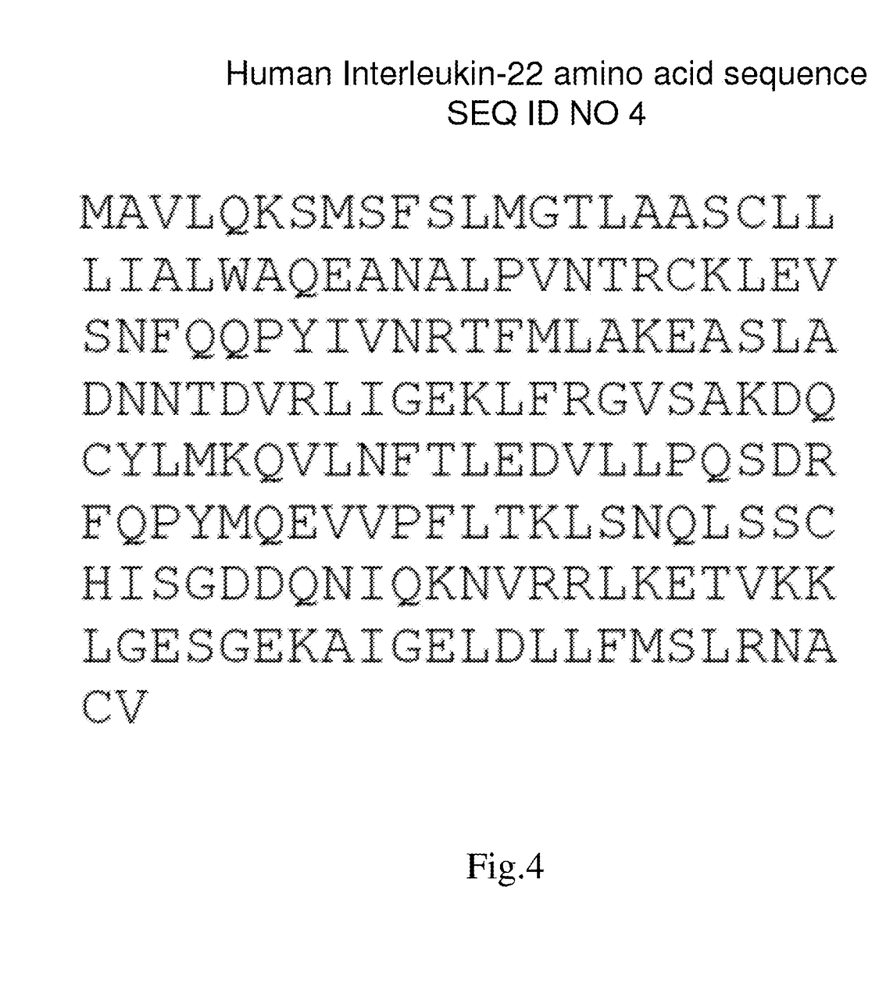
FIG. 4 shows the Human interleukin-22 amino acid sequence.

E. coli strain BL21(+) was used to express the recombinant protein. The E. coli cells were homogenized under high pressure. IL-22 inclusion bodies were obtained by centrifugation and washed with buffers (Tris-HCl 50 mM, NaCl 100 mM, EDTA 1 mM, DTT 1 mM, and sodium deoxycholate 0.5%) completely. Inclusion bodies were solubilized in 8M urea, 50 mM Mes, 10 mM EDTA, and 0.1 mM DTT, pH 6.5. Inclusion bodies was refolded 4 times for 20 hours in 100 mM Tris-HCl, 2 mM EDTA, 0.5 M L-arginine, 1 mM reduced glutathion, and 0.1 mM oxidized glutathion, pH 8. The mixture was then concentrated and purified using a Superdex75 (Amersham) column chromatography. The protein was eluted with 20 mM Tris-HCl, 50 mM NaCl, pH 7. The purity of IL-22 was determined by SDS-PAGE (>95%) as shown in FIG. 3 and FIG. 4. IL-22 protein aliquot was stored at −80° C.

Example 3

Protective Effect of IL-22 on Endotoxin-Induced Sepsis in Mice

Female Balb/c mice, at 6 to 8 weeks, were treated with lipopolysacchride (LPS, *salmonella abortus*-equi (L-5886, Sigma) prepared at 1.0 mg/mL saline. 0.2 mL LPS solution was injected by i.p. to mice at dose of 10 mg/kg Animals were divided to different treatment groups and survival was monitored for 7 days. Single dose of LPS at >12.0 mg/kg could result in 100% animal death at 48 to 72 hrs. LPS dosed at 10 mg/kg single dose resulted in 20 to 30% animal survival by day 7.

Figure 5:
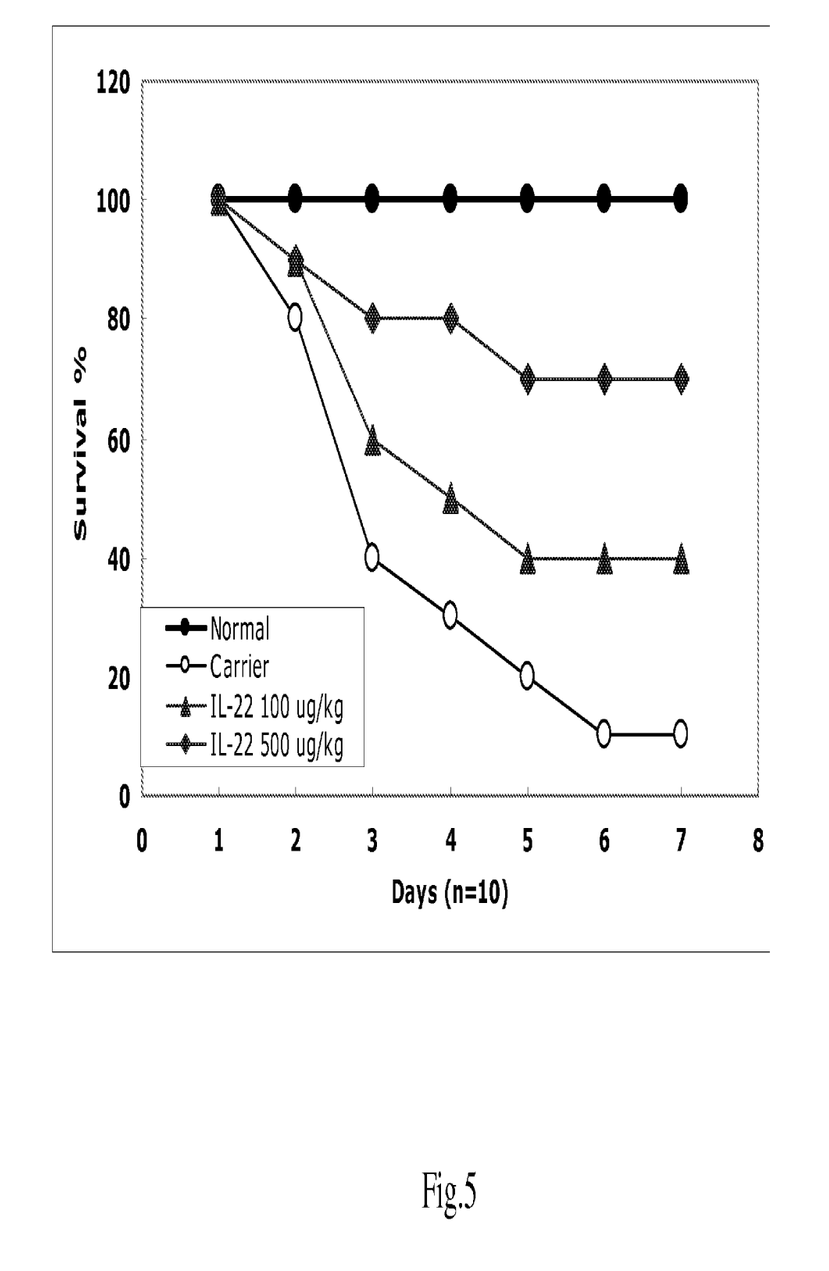
FIG. 5 shows that IL-22 increased animal survival in LPS-induced sepsis shock in mice.

Treatment of mice started with daily subcutaneous injection of recombinant mouse IL-22, at 100 ug/kg, and 500 ug/kg. Control mice were treated with carrier, 0.5% BSA and saline. Results are shown in FIG. 5. Control mice (carrier, n=10) had 20% survival by day 7. Treatment of IL-22 at 100 ug/kg and 500 ug/kg resulted in significant animal survival. These results show that IL-22 significantly protect mice from death in LPS-induced sepsis shock model.

Example 4

Protective Effect of IL-22 on Endotoxin-Induced Multiple Organ Failure in Rats

Animal model of multiple organ failure was established by daily injection of endotoxin (LPS-*E-coli;* 10 mg/kg/day, Difco) to 6 weeks old male Wister rats. Animals were divided into different treatment groups (n=8). Recombinant mouse IL-22 was administered subcutaneously at 100, 300, and 1000 ug/kg/day daily for 7 days. Control animals were injected with carrier solution only, 0.5% BSA PBS, pH 7.0. Serum protein and albumin levels were measured at the end of 7 day treatment.

Figure 6:
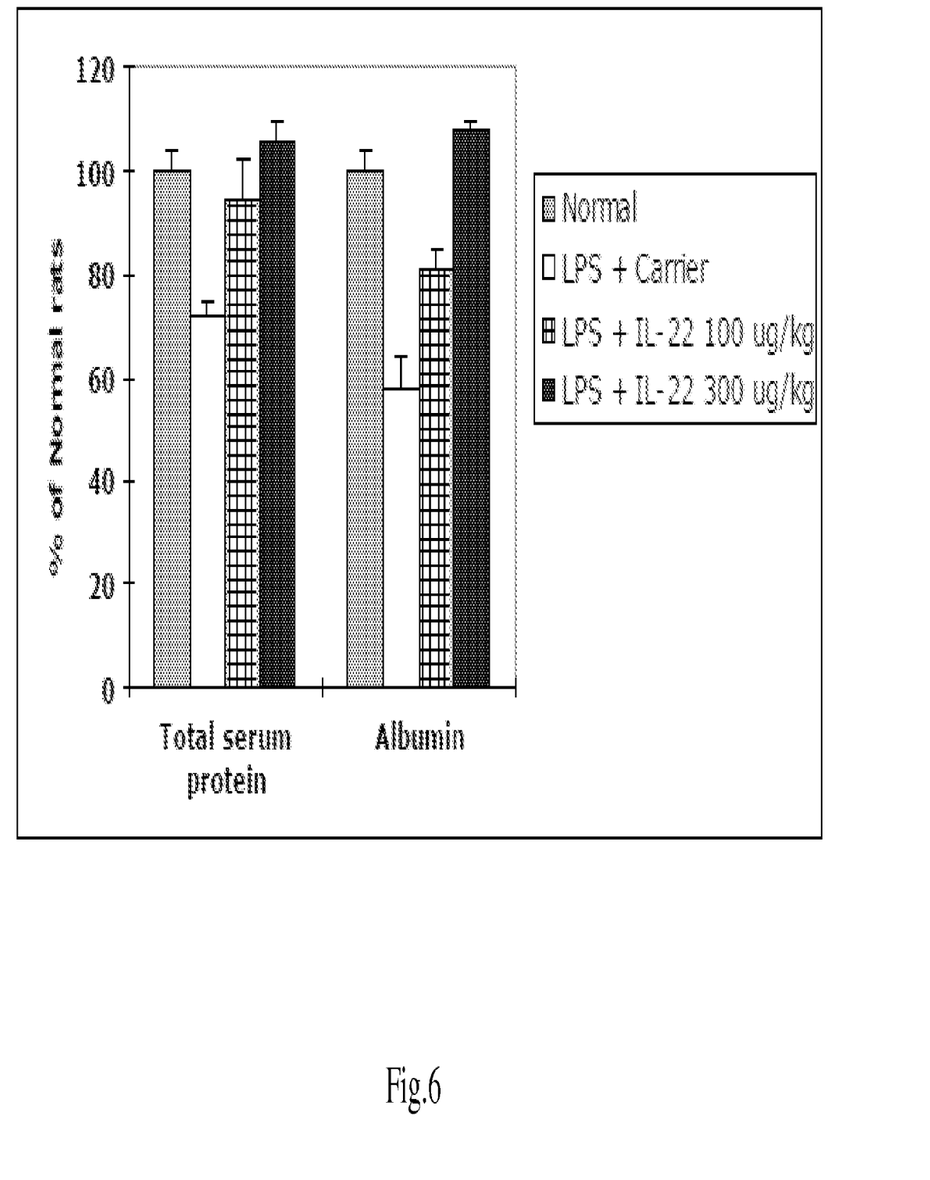
FIG. 6 shows that IL-22 protects LPS-induced multiple organ failure in rats caused by cachexia.

Results are shown in FIG. 6. Serum levels of total proteins, albumin were decreased in control group, indicating that these rats were suffering from cachexia. Animals treated with rmIL-22 had significantly improved blood chemistry parameters. These data shows that IL-22 was effective in protect multiple organ failure in rats caused by endotoxin-induced cachexia.

Example 5

Protective Effect of IL-22 on LPS/GalN-Induced Acute Liver Failure in Mice

Lippolysaccharides (LPS, 100 ng/mL, Sigma, Cat: L2630) and D-galactosamine (D-GalN, 130 mg/mL, Sigma, Cat: G1639) were prepared in pyrogen-free saline. Female BALB/c mice, 6-8 weeks, were injected intraperitoneally (i.p.) with 0.2 mL solution containing 0.1 mL of LPS and 0.1 mL D-GalN. The injection of LPS/GalN into mice induced acute liver failure evidenced by rapid elevation of liver enzymes (>20-fold increase compared to control group) including a greater than 20-fold increase of alanine aminotransferase (ALT) and a greater than 40-fold increase of aspartate aminotransferase (AST) in the serum at 8 hrs. Less than 20% mice were viable at 24 hrs after LPS/GalN challenge.

Figure 7:
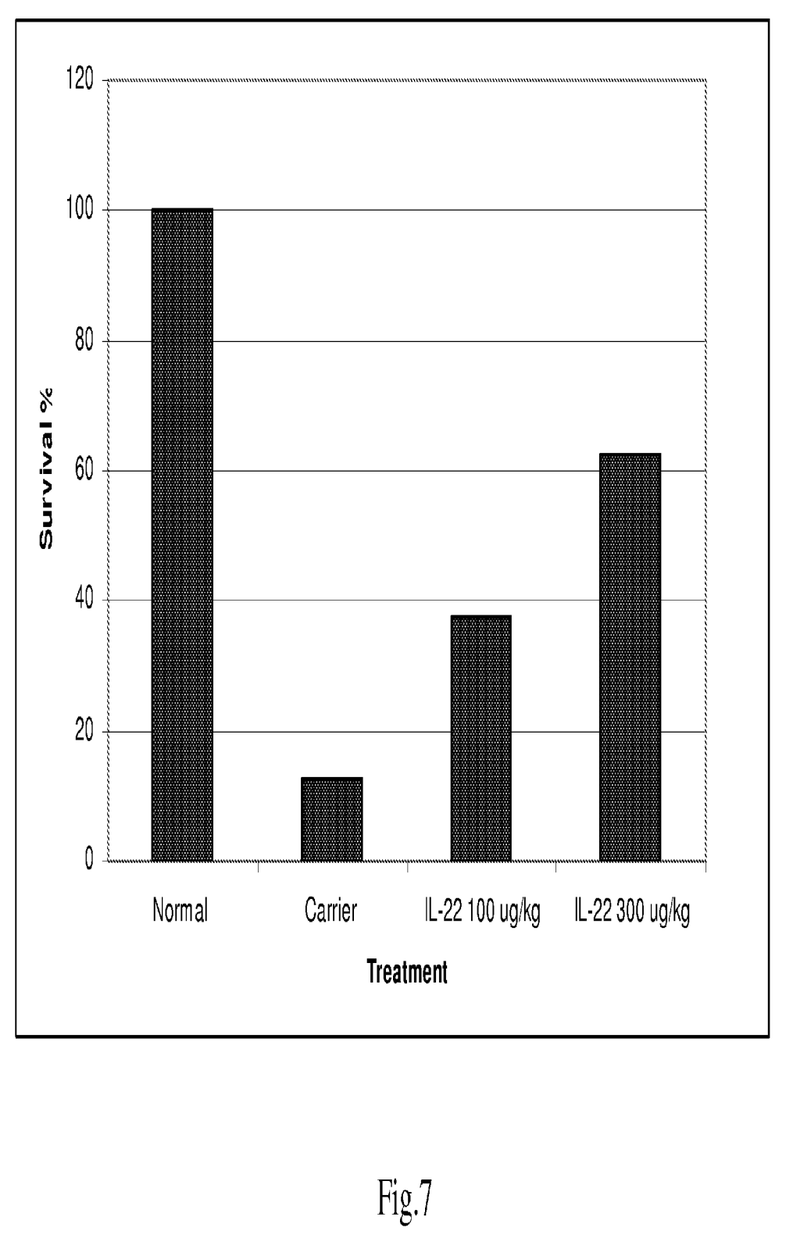
FIG. 7 shows that IL-22 protected animal from death in LPS/GalN-induced acute liver failure in mice.

Treatment of mice started with subcutaneous injection of recombinant mouse IL-22, at 100 ug/kg, and 300 ug/kg. Control mice were treated with carrier, 0.5% BSA and saline. Results are shown in FIG. 7. Control mice (carrier, n=10) had 12.5% survival at 16 hrs. Treatment of IL-22 at 100 ug/kg and 300 ug/kg resulted 37.5% and 62.5% (n=10) survival, respectively. These results show that IL-22 significantly protect mice from LPS/GalN induced death mainly resulted from acute liver failure.

What is claimed is:

1. A method of treatment of sepsis in a subject comprising administering a pharmaceutically effective amount of interleukin-22 (IL-22).

2. The method of claim 1 wherein said IL-22 increases serum total protein in said subject suffering sepsis.

3. The method of claim 1 wherein said IL-22 increases serum albumin in said subject suffering sepsis.

4. The method of claim 1 wherein said IL-22 is mammal IL-22.

5. The method of claim 1 wherein said IL-22 is recombinant mammal IL-22.

6. The method of claim 1 wherein said pharmaceutically effective amount of IL-22 ranges from 100 to 1000 micrograms per kilogram of said subject per day.

7. The method of claim 1 wherein said is endotoxin-induced sepsis.

8. A method of treatment of systemic inflammatory response syndrome in a subject comprising administering a pharmaceutically effective amount of interleukin-22 (IL-22), wherein said pharmaceutically effective amount of IL-22 ranges from 100 to 500 micrograms per kilogram of said subject.

9. The method of claim 8 wherein said IL-22 increases the survival rate of said subject.

* * * * *